United States Patent
Mandecki

(10) Patent No.: US 8,323,886 B2
(45) Date of Patent: Dec. 4, 2012

(54) FLUORESCENCE METHODS OF DETECTING A PROTEIN-ELONGATION RELATED COMPLEX AND COROLLARY SEQUENCE INFORMATION

(76) Inventor: Wlodek Mandecki, Princeton Junction, NJ (US)

( * ) Notice: Subject to any disclaimer, the term of this patent is extended or adjusted under 35 U.S.C. 154(b) by 1057 days.

(21) Appl. No.: 10/871,260

(22) Filed: Jun. 18, 2004

(65) Prior Publication Data

US 2005/0282173 A1 Dec. 22, 2005

(51) Int. Cl.
*C12Q 1/68* (2006.01)
(52) U.S. Cl. ....................................... 435/6.1
(58) Field of Classification Search .................. None
See application file for complete search history.

(56) References Cited

U.S. PATENT DOCUMENTS

| | | | |
|---|---|---|---|
| 5,405,747 | A | 4/1995 | Jett et al. |
| 6,049,380 | A | 4/2000 | Goodwin et al. |
| 6,232,075 | B1 | 5/2001 | Williams |
| 6,306,628 | B1 * | 10/2001 | Rothschild et al. ......... 435/91.3 |
| 6,528,802 | B1 | 3/2003 | Koenig et al. |
| 6,846,638 | B2 * | 1/2005 | Shipwash ...................... 435/7.1 |
| 2006/0228708 | A1 * | 10/2006 | Smilansky ....................... 435/6 |

OTHER PUBLICATIONS

Katunin et al., Coupling of GTP Hydrolysis by Elongation Factor G to Translocation and Factor Recycling on the Ribosome, 2002, Biochemistry, 41, 12806-12812.*

Bustin, Absolute quantification of mRNA using real-time reverse transcription using polymerase chain reaction assays, 2000, J. of Mol. Endocrinology, 35, 169-193.*

Marras et al., Efficiencies of fluorescence resonance energy transfer and contact-mediated quenching in oligonucleotide probes. Nucleic Acids Research, 2002, vol. 30 No. 21 e122, pp. 1-8.*

Selvin, Fluorescence Resonance Energy Transfer, Methods in Enzymology, 1995, vol. 246, pp. 300-334.*

Watson et al., Macromolecular Arrangement in the Aminoacyl-tRNA-Elongation Factor Tu-GTP Ternary Complex. A Fluorescence Energy Transfer Study?, Biochemistry 1995, 34, 7904-7912.*

Truong et al., The use of FRET imaging microscopy to detect protein—protein interactions and protein conformational changes in vivo, Current Opinion in Structural Biology 2001, 11:573-578.*

* cited by examiner

*Primary Examiner* — Christopher M. Babic
(74) *Attorney, Agent, or Firm* — Moser Taboada

(57) ABSTRACT

Provided is an assay method for acquiring sequence information about a single ribonucleic acid, the method comprising: (A) contacting components including a ribosomal particle comprising a ribosome and the ribonucleic acid with a complex comprising moieties that are $aa^1$-tRNA, EF-Tu and GTP or a functional analog, wherein at least one said moiety is labeled with a fluorescent molecule, wherein $aa^1$-tRNA is a tRNA for first amino acid aa1; (B) providing, in conjunction with the contacted components, a ribosomal translation component mixture; (C) generating a fluorescent signal from a labeled moiety in correlation with the incorporation of $aa^1$ into protein and the labeled moiety is thereby separated from the complex; and (D) detecting the signal to provide sequence information about the ribonucleic acid.

19 Claims, 2 Drawing Sheets

FLUORESCENCE METHODS OF DETECTING A PROTEIN-ELONGATION RELATED COMPLEX AND COROLLARY SEQUENCE INFORMATION

BACKGROUND OF THE INVENTION

The present invention relates to methods, reagents and kits to sequence nucleic acids or to determine nucleotide changes in nucleic acids. In particular, the present invention relates to using the ribosome together with protein and nucleic acid components of the cellular ribosomal translation system to acquire nucleic acid sequence information.

The primary sequences of nucleic acids are crucial for understanding the function and control of genes and for applying many of the basic techniques of molecular biology. Sequencing is not only an important tool in genomic analysis but also in other applications, such as genetic identification, forensic analysis, genetic counseling and medical diagnostics. With respect to the area of medical diagnostics, disorders, susceptibilities to disorders and prognoses of disease conditions can be correlated with the presence or absence of particular DNA sequences (or the degree of variation in DNA sequences) at one or more genetic loci. Examples of such phenomena include human leukocyte antigen (HLA) sequence variation, cystic fibrosis, tumor progression and heterogeneity, p53 proto-oncogene mutations and ras proto-oncogene mutations. Recently, a sequence of the whole human genome of $3 \times 10^9$ bp was determined.

Various approaches to sequencing exist. Single molecule DNA analysis methods based on acquiring data from single molecules allow for the gathering of sequence information and generally fall into two categories: (a) the observation of interactions of DNA polymerase, RNA polymerase or exonucleases with DNA, and (b) the measurement of the physical properties of nucleotides in the DNA strand, typically based on ultra high resolution scanned probe microscopy or studies of DNA passing through nanopores (Li et al, Nat Mater 2:611-615 (2003)). Related methods have been described, which include monitoring the incorporation of fluorescently-labeled nucleotides into individual DNA strands by spFRET (Braslavsky et al, Proc Natl Acad Sci USA 100:3960-3964 (2003)) or monitoring of the fluorescently labeled nucleotides released from DNA by an exonuclease in a flow system, or nanopore-based analysis of DNA. Single-molecule DNA analysis can be performed in parallel on a solid support, and, in one implementation, it involves the incorporation of Cy3-labeled reversible chain-terminating dNTP with a cleavable disulfide bond. Sequence information could be derived from thousands of individual DNA molecules spread on a glass slide using a sensitive CCD camera.

Fluorescent dyes have been used in a variety of DNA sequencing techniques. A fluorophore moiety or dye is a molecule capable of generating a fluorescence signal. A quencher moiety is a molecule capable of absorbing the fluorescence energy of an excited fluorophore, thereby quenching the fluorescence signal that would otherwise be released from the excited fluorophore. In order for a quencher to quench an excited fluorophore, the quencher moiety must be within a minimum quenching distance of the excited fluorophore moiety at some time prior to the fluorophore emitting light.

The decreased fluorescence of a fluorophore moiety, a result of a collision or direct interaction with a quencher, is due mainly to a transfer of energy from the fluorophore in the excited state to the quencher. The extent of quenching depends on the concentration of quencher and is described by the Stem-Volmer relationship:

$$F_o/F = 1 + K_{sv}[Q]$$

wherein $F_0$ and $F$ correspond to the fluorescence in the absence and presence of a quencher, respectively, and $[Q]$ is the quencher concentration. A plot of $F_o/F$ versus $[Q]$ yields a straight line with a slope corresponding to the Stem-Volmer constant, $K_{sv}$.

In general, fluorophore moieties have a high quantum yield and a large extinction coefficient so that the fluorescent dye can be used to measure small quantities of the component being detected. Fluorophore moieties preferably have a large Stokes shift (i.e., the difference between the wavelength at which the dye has maximum absorbance and the wavelength at which the dye has maximum emission) so that the fluorescent emission is readily distinguished from the light source used to excite the dye.

Fluorophore-quencher pairs have been incorporated into oligonucleotide probes in order to monitor biological events based on the fluorophore and quencher being separated or brought within a minimum quenching distance of each other. For example, probes have been developed wherein the intensity of the fluorescence increases due to the separation of the fluorophore-quencher pair. Probes have also been developed which lose their fluorescence because the quencher is brought into proximity with the fluorophore. These fluorophore-quencher pairs have been used to monitor hybridization assays and nucleic acid amplification reactions, especially polymerase chain reactions (PCR), by monitoring either the appearance or disappearance of the fluorescence signal generated by the fluorophore molecule.

A need exists for acquiring data related to sequences of nucleic acid by determining positions of certain codons along the polynucleotide chain. Therefore, a need exists for a fluorescent molecule which senses a nucleic acid sequence with high nucleotide specificity, without getting incorporated into the nucleic acid. These and further needs are met by the present invention. Benefits and advantages of the present invention include quick readout, use of very small quantities of reagents, capabilities for parallel readout, and low cost of the assay with a wide applicability to many laboratory procedures, diagnostics and drug discovery.

SUMMARY OF THE INVENTION

To achieve the foregoing and other aspects of the invention and in accordance with the purposes set forth herein, the present invention is directed to an assay method for acquiring sequence information about a single nucleic acid molecule, the components of the assay comprising a complex having two moieties, at least one moiety labeled with a fluorescent molecule. The method comprises the steps of illuminating the complex to excite the fluorescent molecule, bringing into contact the complex and the single nucleic acid molecule and causing the complex to recognize the single nucleic acid molecule, generating a fluorescence signal, detecting the fluorescence signal, and deducing from the fluorescence signal sequence information about the single nucleic acid molecule.

In another aspect of the invention, an assay method for acquiring sequence information about a single nucleic acid molecule is provided. The components of the assay comprise a complex having two moieties. One moiety is labeled with a fluorescent molecule and the other moiety is labeled with a quencher molecule. The quencher molecule is sufficiently proximal to the fluorescent molecule to quench the fluorescence of the fluorescent molecule The method comprises the steps of illuminating the complex to excite the fluorescent molecule, bringing into contact the complex and the single nucleic acid molecule and causing the complex to recognize the single nucleic acid molecule, and generating a fluorescence signal. The fluorescence signal is detected and the fluorescence signal sequence information about the single nucleic acid molecule is deduced.

In one aspect of the invention, the single nucleic acid molecule is RNA, and the complex recognizes a codon on the mRNA. The fluorescence signal corresponds to the recognition of a codon on the mRNA and one or more fluorescence signals define a pattern characteristic of the mRNA. One moiety is aa-tRNA, the other moiety is EF-Tu. The complex recognizes the mRNA during an elongation reaction on a ribosome.

In one aspect of the invention, the RNA molecule interacts with a ribosomal translation component mixture comprising EF-Tu, tRNA and GTP. One or more EF-Tu, tRNA and GTP are labeled with a fluorescent molecule. The ribosomal translation component mixture is illuminated to excite the fluorescent molecule, the fluorescence signal is detected, and the sequence information is deduced from the fluorescence signal. The EF-Tu and two or more different aa-tRNA's form two or more complexes, and the two or more complexes are labeled with two or more fluorescent molecules having distinguishable fluorescence properties.

A probe and kit for performing the assay of the invention are also provided. The probe and kit comprise a complex having two moieties. One moiety is labeled with a fluorescent molecule and the other moiety can be labeled with a quencher molecule. The kit further comprises a ribosomal translational component mixture.

Figure 1:
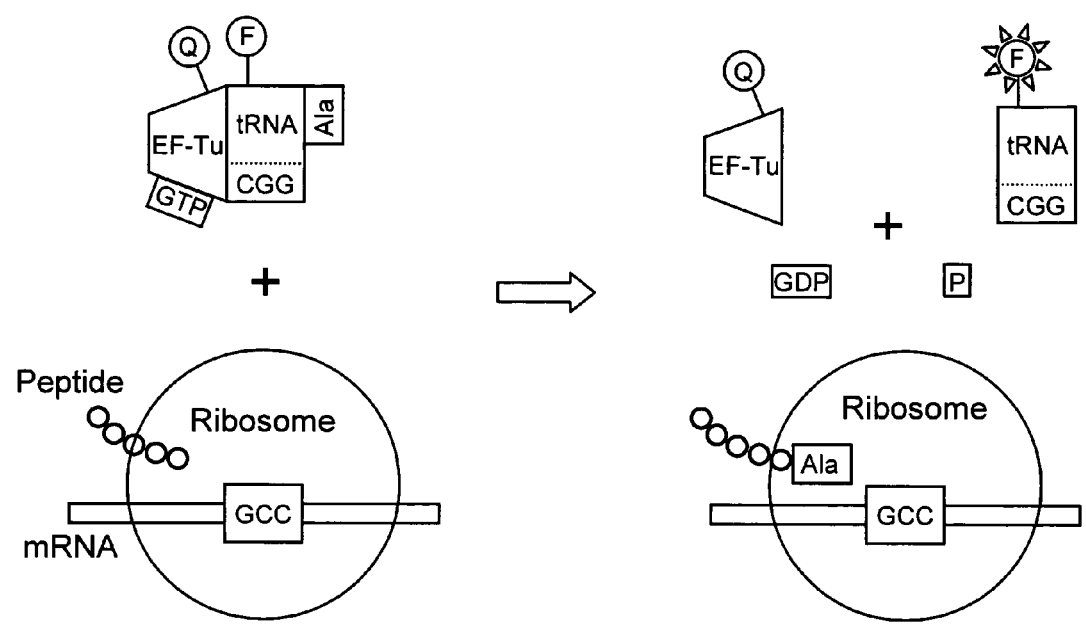
FIG. 1 is an illustration of the method of the invention.

So that the manner in which the above recited features of the present invention can be understood in detail, a more particular description of the invention, briefly summarized above, may be had by reference to embodiments, some of which are illustrated in the appended figures. It is to be noted, however, that the appended drawings illustrate only typical embodiments of this invention and are therefore not to be considered limiting of its scope, for the invention may admit to other equally effective embodiments.

Definitions

The term "aa-tRNA", or "aminoacyl tRNA", refers to the name of the complex created when a tRNA molecule is covalently attached to its specific amino acid and ready to participate in protein synthesis.

The terms "anticodon" refers to the three-base sequence in tRNA complementary to a codon on mRNA. The term "anticodon" shall also refer to a nucleotide triplet in a tRNA molecule that aligns with a particular codon in mRNA under the influence of the ribosome, so that the amino acid carried by the tRNA is added to a growing protein chain.

The term "codon" refers to a section of DNA (three nucleotide pairs in length) or RNA (three nucleotides in length) that codes for a single amino acid. The term "codon" shall also refer to a sequence of three RNA or DNA nucleotides that specifies (codes for) either an amino acid or the termination of translation.

The term "EF-Tu", or "elongation factor Tu", refers to a protein translation factor in eubacteria. This protein promotes the GTP-dependent binding of aminoacyl-tRNA to the A-site of ribosomes during protein biosynthesis. The protein with an equivalent function is named EF-1α in archaebacteria and eukaryotes.

The term "fluorescence" refers to an optical phenomenon in which a molecule absorbs a high-energy photon and re-emits it as a lower-energy (longer-wavelength) photon, with the energy difference between the absorbed and emitted photons ending up as molecular vibrations or heat.

The term "fluorescence correlation spectroscopy (FCS)" refers to a technique in which spontaneous fluorescence intensity fluctuations are measured in a microscopic detection volume of about $10^{-15}$ L (1 femtoliter) defined by a tightly focused laser beam. The fluorescence intensity fluctuations measured by FCS represent changes in either the number or the fluorescence quantum yield of molecules resident in the detection volume.

The term "fluorescence resonance energy transfer (FRET)" refers to a distance-dependent interaction between the electronic excited states of two dye molecules in which excitation is transferred from a donor molecule to an acceptor molecule without emission of a photon. Often, the energy transfer is followed by the emission of light at a longer wavelength. The efficiency of FRET is dependent on the inverse sixth power of the intermolecular separation, making it useful over distances comparable with the dimensions of biological macromolecules.

The term "fluorescent molecule" refers to a molecule or an aggregate of molecules (for example, a nanoparticle or quantum dot) capable of fluorescence.

The term "guanosine triphosphate nucleotide" or "GTP" refers to a molecule which consists of the nitrogenous base guanine linked to the sugar ribose and which has three phosphate groups attached to the 5th carbon atom of the ribose. GTP is a high-energy compound which serves as an energy source for many biochemical reactions. The energy source is required for the formation of peptide bonds between amino acids during translation and for ribonucleic acid synthesis since it is a direct precursor.

The term "mRNA", or "messenger RNA", refers to an RNA molecule transcribed from the DNA of a gene, and from which a protein is translated by the action of ribosomes. The basic function of the nucleotide sequence of mRNA is to determine the amino acid sequence in proteins.

The term "quencher molecule" refers to a molecule or an aggregate of molecules such as a nanoparticle capable of quenching.

The term "quenching" refers to a process which reduces or quenches the fluorescence intensity from a fluorescent dye. The term "fluorescence quenching" refers to a bimolecular process that reduces the fluorescence quantum yield without changing the fluorescence emission spectrum. Fluorescence quenching can result from transient excited-state interactions, or collisional quenching, or from the formation of non-fluorescent ground-state species.

The term "quenching efficiency" refers to a degree by which fluorescence intensity (FI) is reduced by the quencher. Quenching efficiency can be expresses as the ratio of the fluorescence intensity (FI) in the presence of the quencher to the fluorescence intensity (FI) in the absence of the quencher.

The term "RNA" or "ribonucleic acid" refers to an organic acid composed of repeating nucleotide units of adenine, guanine, cytosine and uracil. The ribose components of the nucleotide units are linked by phosphodiester bonds. There are several classes of RNA molecules, including messenger RNA, transfer RNA, ribosomal RNA and other small RNAs, each serving a different purpose.

The term "ribosomal translation component mixture" refers to an assembly of ribosomes, proteins, protein factors and small molecules needed for ribosomal translation reaction. Generally, the ribosomal translation component mixture is configured as a concentrated solution of components in a buffer.

The term "ribosome" refers to a small cellular component composed of specialized ribosomal RNA and protein within the cytoplasm of the cell. The ribosome is the site where protein synthesis takes place. One or more ribosomes attach to mRNA and travel along its path one codon at a time, and stop along its path until a tRNA fetches the required amino acid. When a ribosome reaches a stop codon, the complex releases the completed protein molecule for use by the cell.

The term "sequence information" refers to data related to nucleotide sequences of nucleic acids (DNA or RNA) or amino acid sequences of proteins. The sequence information can be complete, such as nucleic acid or protein sequences, or partial, such as positions of given nucleotides or amino acids within the DNA/RNA or protein, respectively.

The term "spFRET", or "single pair FRET", refers to a fluorescence measurement of energy transfer between a single donor and a single acceptor. SpFRET is useful for studying intramolecular conformational changes (for example, between donor and acceptor when the two are attached to two different sites on the same macromolecule), and intermolecular interactions (for example, when the donor is attached to one macromolecule and the acceptor is attached to a second molecule).

The term "tRNA" or "transfer RNA" refers to a short chain RNA molecules which are present in the cell. Generally, there are at least 20 varieties; each variety is capable of combining with a specific amino acid and attaching the correct amino acid to the protein chain that is being synthesized at the ribosome. Such synthesis is carried out in accordance with the genetic information coded in the mRNA.

The term "translation" refers to a process in which the genetic code carried by messenger RNA directs the synthesis of proteins from amino acids. Translation can occur either in the cell (in vivo), or in a cell-free system, that is, (translation).

The term "wobble" refers either to the potential of a single tRNA to bind to two or more codons or to the ability of certain bases at the third position of an anticodon in tRNA to form hydrogen bonds in various ways, causing alignment with several possible codons, thus leading to a reduced constraint of the third base of an anticodon as compared with the other bases thus allowing additional complementary base pairings.

DETAILED DESCRIPTION

The present invention provides an assay method for the acquisition of sequence information about a single nucleic acid molecule. The nucleic acid molecule is recognized by a complex having two moieties. In one aspect of the invention, one moiety can be labeled with a fluorescent molecule and the other moiety can be labeled with a quencher molecule. The quencher molecule is located sufficiently proximally to the fluorescent molecule to quench the fluorescence of the fluorescent molecule. One moiety is a nucleic acid molecule and the other moiety is an elongation factor. The quencher has the property of significantly reducing the fluorescence of the fluorescent molecule. As the single molecule is recognized, the moieties separate thus increasing the distance of the fluorescent molecule and the quencher molecule, and a fluorescence signal is generated. The fluorescence signal is indicative of the recognition of a codon in the single nucleic acid molecule. The quenching efficiency may be between at least about 2-fold to about 100-fold (from about 50% to about 99%) and may vary depending on the distance between the fluorescent molecule and the quencher molecule, the chemical composition and molecular properties of both. The quenching efficiency may be influenced by the chemical purity and homogeneity of the complex.

Without departing from the spirit of the invention, in another aspect of the invention, a quencher molecule may not be required and a moiety can be labeled with a fluorescent molecule. As the single molecule is recognized, the moieties separate, and a fluorescence signal is generated. As stated above, the fluorescence signal is indicative of the recognition of a codon in the single nucleic acid molecule.

Several quenching mechanisms exist. In certain instances, the quenching depends on spectral overlap between the fluorescent molecule and the quencher molecule, and it functions at a long range (fluorescence resonance energy transfer, FRET). In other instances, the fluorescent molecule and the quencher molecule interact between molecular orbitals and require contact between the fluorescent molecule and the quencher molecule, for example by electron transfer mechanisms. In still other instances, a ground-state complex quenching mechanism can occur. All such quenching mechanisms are within the scope of the present invention, and quenching mechanisms that provide for a high quenching efficiency are especially advantageous for reducing the background fluorescence, thus contributing to an improvement in the accuracy of the readout and permitting the use of higher concentrations of reagents.

There is a great deal of practical guidance available in the literature for providing an exhaustive list of fluorescent and chromogenic molecules and their relevant optical properties and on derivatizing fluorescent and quencher molecules for covalent attachment via common reactive groups that can be added to a nucleotide, as exemplified in U.S. Pat. No. 6,232, 075.

In one aspect of the invention, the fluorescent molecule is a fluorescent organic dye derivatized for attachment to the complex directly or via a linker. Preferably, quencher molecules are also organic dyes, which may or may not be fluorescent, depending on the particular embodiment of the invention. For example, in one aspect of the invention, the fluorescent molecule and the quencher molecule are both fluorescent, and a fluorescence energy transfer mechanism can be used wherein the first fluorophore is excited and emission is read from the second fluorophore.

Suitable donors and acceptors operating on the principle of fluorescence energy transfer (FRET) include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethylcoularin (Coumaran 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)$_4$-methylcoumarin; diethylenetriaamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'dimethoxy-4'5'-dichloro-6-carboxy-fluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalo cyanine; and naphthalo cyanine.

With applicability to the invention, fluorophore-quencher pairs include, but are not limited to, xanthene dyes (including fluoresceins), and rhodamine dyes. Many suitable forms of these compounds are widely available commercially with substituents on their phenyl moieties which can be used as the site for bonding or as the bonding functionality for attachment to the gamma-phosphate or nucleobase. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-toluidinyl-6-naphthalene sulfonate. Other dyes include 3-phenyl-7-isocyanatocoumarin, acridines, such as 9-isothiocyanatoacridine and acridine orange, N-(p-(2-benzoxazolyl)phenyl)maleimide, benzoxadiazoles, stilbenes, pyrenes, and the like. The fluorophore-quencher pair may be selected from fluorescein and rhodamine dyes. These dyes and appropriate linking methodologies for attachment to nucleotides are exemplified in U.S. Pat. Nos. 5,188,934 and 5,366,860.

In one aspect of the invention, the single nucleic acid molecule is an mRNA and the complex is an aa-tRNA bound to elongation factor Tu (EF-Tu). The aa-tRNA molecule is labeled with a fluorescent dye molecule, and EF-Tu is labeled with a quencher molecule having the property of reducing the fluorescence of the dye molecule, if both the fluorescent molecule and the quencher molecule are proximally located. The quenching efficiency is from at least about 2-fold to about 100-fold.

According to the method, during the process of elongation of a growing polypeptide chain, a codon in the mRNA molecule bound to the ribosome is recognized by a complex of a cognate aa-tRNA bound to elongation factor Tu (EF-Tu). As the codon is recognized by this complex, EF-Tu is released and aa-tRNA participates in peptide elongation on the ribosome. Continuation of the process is dependent on GTP hydrolysis and another protein factor, EF-G.

The method of the invention is illustrated in FIG. 1. The ribosome is represented as a circle; EF-Tu, as a trapezoid; and tRNA as a rectangle showing the anticodon and amino acid with which the tRNA is charged with. The nucleotides, GTP and GDP, and phosphate P are also indicated. The aa-tRNA molecule is labeled with a fluorescent dye molecule, F and EF-Tu is labeled with a quencher molecule Q having the property of reducing significantly the fluorescence of the dye molecule when both the dye and the quencher molecule are in immediate proximity. As shown in FIG. 1, upon the binding reaction of the EF-Tu-tRNA complex, followed by codon recognition and the formation of the peptide bond, EF-Tu and tRNA separate, The fluorescent molecule and the quencher molecule are no longer in proximity and a fluorescence signal is generated by reversing the quenching effect of the quencher molecule on the fluorescent molecule.

Before the elongation reaction takes place, a complex is formed comprising two moieties. One moiety is a specific aa-tRNA labeled with a fluorescent dye F [aa-tRNA-F]. The other moiety an elongation factor EF-Tu labeled with a quencher molecule Q [EF-Tu-Q]. The complex is referred to as [aa-tRNA-F:EF-Tu-Q] and can be added to a translation mixture comprising all necessary molecular components for elongation, including but not limited to initiation factors, elongation factors EF-G and EF-Ts, and ribosomes as set forth in Example 10. As shown in FIG. 1, when the codon on the mRNA molecule is recognized, aa-tRNA-F and EF-Tu-Q separate, and the amino acid is incorporated into the growing polypeptide chain. The tRNA is not released from the ribosome until one more amino acid are added to the peptide chain due to migration from the ribosomal A site to the P and then E sites on the ribosome during translocation. Since the fluorescent dye F is no longer in the immediate proximity of the quencher molecule Q, the fluorescence signal from the dye F increases greatly and is measured by a fluorescence detector. The detector can be any detector capable of acquiring fluorescence from sub-femtoliter volumes. Typical detectors include a fluorescent microscope-based FCS-capable spectroscopy system.

Figure 2:
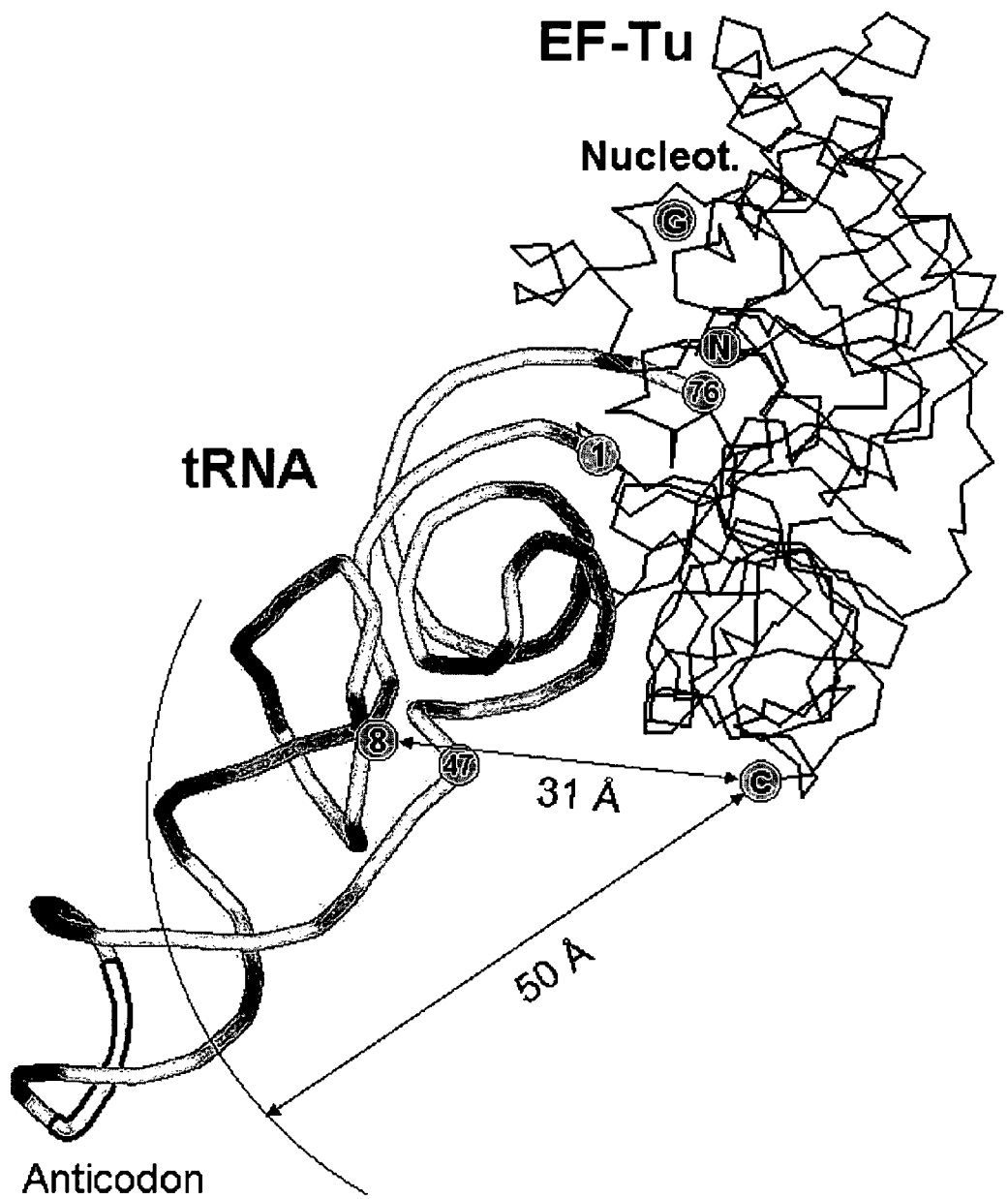
FIG. 2 is an illustration of the complex of aa-tRNA and EF-Tu.

FIG. 2 is an illustration of the complex of aa-tRNA and EF-Tu. FIG. 2 shows the crystal structure of the ternary complex of Phe-tRNA$^{Phe}$ from yeast with EF-Tu from *T. aquaticus* and a GTP analog, GDPNP (Nissen et al, Science 270: 1464-1472 (1995)). The GTP analog is indicated with a symbol "Nucleot." and the position of the alpha phosphate atom is labeled with the letter "G." The C- and N-terminal residues of EF-Tu are labeled with the letters "C" and "N" respectively. The approximate position of certain nucleotides in tRNA is indicated with numbers. A portion of the tRNA molecule within a distance of 50 Å from the C-terminal residue of EF-Tu is indicated with an arc. The anticodon is highlighted with a thick line. Without limitation, nucleotide 8 and nucleotide 47 are possible labeling sites.

In one aspect of the invention, a single tRNA in the complex may be labeled with a fluorescent dye. An example of a tRNA molecule includes, without limitation, Ala-tRNA$_{CGG}$, or any other tRNA charged with an amino acid. The mRNA molecule includes a number of codons which can be recognized by more than one type of tRNAs. When an mRNA molecule is brought into contact with the complex, a series of fluorescence signals can be observed as a function of time, with each signal corresponding to a recognition of the GCC codon on the mRNA by the tRNA. The time interval between each signal is roughly proportional to the distance between two adjacent GCC codons (although stochastic variation will be observed due to randomness of molecular recognition; another cause of variation is unequal translation speed of the codons between the GCCs). A pattern of signals is characteristic of a given mRNA sequence and can be used to recognize different mRNA sequences by analyzing the time intervals between different fluorescence signals and comparing the data to possible patterns expected from the known nucleotide sequence(s) of mRNA.

The method is scalable with respect to the number of tRNA molecules labeled with one or more fluorescent dye. Using an optical detector which is capable of detecting a signal at two or more wavelengths, the method of the invention is amenable to providing information about the position of two or more types of codons on the mRNA. Specifically, if all 31 tRNA specificities are labeled in an orthogonal fashion, and the optical detector is capable of distinguishing all 31 types of signals, the data acquired will enable the complete assignment of tRNA species to the consecutive codons in mRNA. The result of such analysis can lead to the determination of the nucleotide sequence with the exception of wobble positions in codons. With 61 coding codons and the assignment of 61 uniquely labeled tRNAs, the analysis may lead to the equivalent of a complete nucleotide sequence of the coding region on the mRNA.

In one aspect of the invention, a quencher molecule such as a poly-azo or poly-aromatic compound (for example BHQ-10, Biosearch Technologies, Novato, Calif.) can be used. The quencher molecule BHQ-10 is commonly used in FRET assays and quenches fluorescence from a wide variety of fluorescence dyes which emit between about 450 nm and about 550 nm. Without being bound by any particular theory, it is believed that the quenching mechanism involves transfer of energy from the fluorescent label to the quencher molecule, followed by the dissipation of energy as heat or molecular vibrations. In another aspect of the invention, the quencher molecule 4-(4-dimethylaminophenylazo)benzoyl (DABCYL) and gold nanoparticles can be conjugated to a protein or DNA and thus function as a quencher molecule.

Linking moieties and methodologies have been used for attaching a fluorescent or quencher molecule to a nucleotide, nucleic acid or protein, as exemplified by experimental methods and protocols in a handbook provided by Molecular Probes Inc. (www.probes.com/handbook). In one aspect of the invention, the quencher molecule can be attached by conjugating the quencher molecule to different chemical moieties, such as a linker. Example of such linkers are set forth in the Molecular Probes Handbook and include without limitation the succinamide group, the isoshiocyanate group, (for example fluorescein isothiocyanate), the sulfonyl chloride group (for example Texas Red sulfonyl chloride), the aldehyde group (for example o-phtaldialdehyde), the maleimide group (for example nanogold maleimide or QSY7 maleimide), to name a few. The quencher molecule may be derivatized with the linker and may be attached via the linker, provided that the linkage linking the quencher molecule and the nucleotide do not quench the fluorescence of the fluorescent molecule.

The quenching efficiency is a routine parameter easily determined. As will be apparent to those of skill in the art, the quenching efficiency can be measured in a fluorometer. A fully fluorescent dye has a $F_o$ value of 1, whereas a dye quenched by 90% has an F value of 0.100. A compound quenched by 90%, has a quenching efficiency of 0.9 or is 10-fold quenched. For the fluorescent label-quencher pairs of the present invention, the quenching efficiency is between about 1.5-fold to about 1,000-fold. In one aspect of the invention, the quenching efficiency is about 2-fold to about 10-fold, and from about 3-fold to about 100-fold.

The method has many applications including, without limitation, real-time monitoring of the progression of translation at the level of a single molecule, the determination of ribosomal frame-shifting, the determination of the effects of the mRNA secondary structure on the translation, the analysis of the behavior of the ribosome at the frame shifting sites, particularly pausing by monitoring the time course of elongation, the incorporation of non-natural amino acids into proteins, including the kinetics of incorporation at the single-molecule level, the measurement of the translation rates for different nucleotide segments on the same mRNA molecule and the study of the interaction of the protein and nucleic acids with the mRNA molecule.

In one implementation of the invention, the sequence information from the mRNA can be collected by parallel readout of signals from many ribosomal particles. Parallel readout enables ultra-fast expression profiling, by determining the actual numbers of different types of mRNA molecules, in very small samples, including individual cells (the number of mRNA molecules in a single cell is on the order of $2\times10^5$ to $10^6$, compatible with the anticipated level of parallel detection). Parallel readout finds applicability in areas such as diagnostics, and drug discovery.

The method of the present invention makes it suitable for nucleic acid sequencing. The path to sequencing is through increasing the number of labeled tRNA species and the development of fluorescence detection methods compatible with single molecules and multiple labels plus the parallel readout. An ability to label and detect 31 tRNA species (for example from E. coli) would be equivalent to a sequencing capability. All amino acid residues can be assigned to the codons, thus providing a useful method for identifying nucleotide sequence changes which may be indicative of mutations in proteins. An assay based on 31 tRNAs may or may not require 31 different fluorescent molecules. In certain assay designs, 5 molecules and 10 or 11 separate translation reactions might suffice.

Another application of the present invention may be in low-cost sequencing of the genome, on the order of $1,000 or less per genome. The cost of reagents may be minimized and the turnaround time may be shortened. The mRNA sequencing method may be designed to sequence cellular transcripts, or to sequence any DNA or RNA, including genomic DNA. To circumvent the presence of stop codons and the lack of transcription signals in non-mRNA nucleic acid, suppressor tRNAs may be used in the translation system. In addition, the transcription signals may be introduced by PCR, and mRNA maybe made in a T7 transcription system, such as, for example, the system for sample preparation method for genotyping and expression profiling provided by Affymetrix, Inc. (Santa Clara, Calif.).

The present invention provides the capability of low cost genomic sequencing. Based on a translation rate of about 10 codons/sec (i.e., 30 nt/sec), one data collection channel, if used to capacity, can provide up to $10^6$ sequence data points in about 24 hrs. With an anticipated 100× redundancy, (a 10× factor to provide adequate statistics and an additional 10× factor associated with the use of a limited number of colors [five]), collecting data in $3\times10^5$ channels may prove sufficient for a whole genome sequencing. A number of channels of $3\times10^5$, is compatible with current capabilities (number of pixels) of ultra-sensitive CCD cameras.

The present invention finds applicability in the analysis of nucleic acids of diagnostic or pharmaceutical significance. In particular, the present invention can be used to analyze abnormalities associated with nucleic acids, such as mutations, single nucleotide polymorphisms, the identification of infectious agents (viruses, bacteria, microorganisms, others), the analysis of cancer-related genetic material, and the performance of prenatal diagnosis to list a few.

One advantage of the present invention is that labeling of the single molecule is not required. Fluorescence labeling of the building blocks (nucleotides) within the polymer being sequenced (DNA, RNA) is also not required. Furthermore, since the present invention is based on specific sequence recognition and the ribosome error rate during elongation is about $10^{-4}$ per amino acid, excellent accuracy of the present assay is assured. Another advantage of the present invention is that there is no requirement for fluidics readout.

Another advantage of the invention is that photobleaching can be minimized as the dye is exposed to light only when the tRNA-F:EF-Tu-Q approaches the ribosome. After the productive recognition of the codon, the dye diffuses out as tRNA-F and does not participate in further biosynthesis. This is in contrast to a dye incorporated into a biomolecule which is studied over time while it is exposed to light. Yet another advantage is that mRNA is sequenced, which is advantageous over the sequencing of DNA especially in applications requiring data related to protein sequence or protein expression in mammalian systems, wherein RNA processing (for example: splicing, editing) is frequent.

One characteristic of the invention is the minimal requirements for sample preparation. A simple sample preparation method should suffice in a future multichannel instrument in which many mRNAs are analyzed at a time. It has been demonstrated that sample preparation in less critical in spFRET than in the ensemble-type procedures (Wabuyele et al, J Am Chem Soc. 125:6937-6945 (2003)). Another characteristic of the invention is real-time molecular analysis as compared to nucleic acid analyses which take a long time to complete due to the need of using serially or in parallel methods such as PCR, hybridization and gel electrophoresis. Another characteristic is that the method of the invention provides for fast acquisition of data and has a high degree of processivity. The rate of sequence acquisition may be about 30 nt/second/channel. This is about three orders of magnitude faster than the dideoxy method of DNA sequencing. The speed of the present is an advantageous characteristic. And there is no limit on how many codons can be read by a single ribosome particle after a single translation initiation event.

I. Methods

Key Reagents

According to the present invention, both tRNA and EF-Tu are derivatized with small molecule dyes for the translation reaction and FRET assay. FRET is a distance-dependent interaction between the electronic excited states of two dye molecules in which excitation is transferred from a donor molecule to an acceptor molecule without the emission of a photon. The efficiency of FRET is dependent on the inverse sixth power of the intermolecular separation, making it useful over distances comparable with the dimensions of biological macromolecules. The distance at which energy transfer is 50% efficient (i.e., 50% of excited donors are deactivated by FRET) is defined by the Förster radius ($R_o$). The magnitude of $R_o$ is dependent on the spectral properties of the donor and acceptor dyes. Typical values of $R_o$ are 55 Å for the fluorescein-tetramethylrhodamine donor-acceptor pair, 57 Å for the BODIPY-FL-BODIPY-FL pair, or 61 Å for the fluorescein and QSY7 (or QSY9) pair (Wu and Brand, Anal Biochem 218: 1-13 (1994)). For comparison, the *Escherichia coli* ribosome is 250 Å across in the largest dimension, EF-Tu-57 Å, and tRNA-76 Å.

In the FRET assay, geometrical localization of the dyes was considered. An analysis was performed of distances between possible positions of the dyes in the EF-Tu:tRNA complex. The analysis was based on the crystal structure of a complex of yeast Phe-tRNA$^{Phe}$ and *Thermus aquaticus* EF-Tu (Nissen et al, Science 270:1464-1472 (1995)) and represented in FIG. 2. As the amino acid sequences of both EF-Tu and tRNAs from bacteria and yeast are highly homologous, this crystal structure is an approximation of the structure of bacterial complexes.

The 50 Å region around the C-terminus (CA atom of residue 405) is shown in FIG. 2. The great majority of residues in the tRNA molecule is located within this region. The residues are appropriate targets for conjugation of the fluorescent dye, with the exception of the anticodon-proximal region. In particular, the 5'-terminal residue (P atom) is 25 Å away, and the 3'-terminal residue (P atom) 40 Å away from the C-terminus. All atoms in EF-Tu are less than 60 Å from both 5' and 3' ends of tRNA and the distances between the N-terminus of EF-Tu and the tRNA's 3' and 5' ends are 8 Å and 25 Å, respectively. Thus, the distances between relevant regions in both EF-Tu and tRNA are sufficiently small to enable the configuration of an efficient FRET assay.

tRNA

A variety of protocols have been developed for labeling tRNA molecules. In such labeling, a chemically active functional group on a tRNA molecule participates in a chemical reaction with a suitable form of a dye or nanoparticle. Examples of active groups include thiol or primary amino groups.

Most *E. coli* tRNAs carry a uridine to 4-thiouridine modification at a position homologous to position 8 of tRNA$^{Phe}$ of *E. coli*. Extensive binding studies were performed on tRNA$^{Phe}$ fluorescently labeled at a 4-thiouridine base at that site, position 8 ($s^4$U-8) (see FIG. 2), and all aa-tRNAs modified and examined were biologically active in translation. In particular, the tRNAs were capable of binding to EF-Tu-GTP and supported transpeptidation and, therefore, translocation to the P site indicating that $s^4$U-8 position in tRNA is suitable for derivatization according to the present invention (Adkins et al, Biochemistry, 22:1208-1217 (1983)).

Many tRNAs carry another modification at the position homologous to position 47 of *E. coli* tRNA$^{Phe}$. This position can be labeled with the nanoparticle, undecagold. Undecagold is a 6,200 da cluster of gold (Au11, particle diameter of 0.8 nm) known to be a very efficient fluorescence quencher (extinction coefficient $\epsilon_{420}$ of 47,000). It was used in the art to label 3-(3-amino-3-carboxypropyl) uridine ($acp^3$-U) at position 47 of tRNA$^{Phe}$ from *E. coli* (Blechschmidt et al, Eur J Biochem 219:65-71 (1994)). Significantly, Au11-labeled Phe-tRNA$^{Phe}$ forms a ternary complex with EF-Tu and is active in poly(U)-dependent poly-Phe synthesis. Thus, tRNA can be labeled with nanoparticles while its biological activity is preserved. The distance between residue 47 (P atom) in tRNA$^{Phe}$ and EF-Tu's C-terminus is 29 Å (FIG. 2), quite suitable for the FRET assay. Ten out of 45 *E. coli* tRNAs in the tRNA database carry $acp^3$-U at the homologous position (www.uni-bayreuth.de/departments/biochemie/sprinzl/trna/index.html). The labeling protocol is set forth in Example 3.

Other approaches to tRNA labeling can be used. In these approaches, the 3' ends of tRNA are charged (residue 76 in FIG. 2) with a fluorescent form of the amino acid, as described in Example 2. The 5' end and, in particular, the phosphate group at the 5' end can be labeled as well. Selected methods for labeling tRNA are set forth in Examples 1-3.

EF-Tu

Stable species of EF-Tu are utilized because of their enhanced stability in a prolonged conjugation procedure and experimentation. Work has been done on thermostable EF-Tu from *Thermus thermophilus*, a protein of 405 amino acids. The gene was overexpressed in *E. coli*, the crystal structure determined and the protein was subjected to a number of site-directed mutagenesis studies. Together with analogous studies of highly homologous *E. coli* EF-Tu (about 75% sequence identity) and *Thermus aquaticus* EF-Tu (98% sequence identity when compared to the *T. thermophilus* EF-Tu), the role of different regions has been determined. The C-terminus of EF-Tu is quite insensitive to additions of several amino acid residues comprising a $His_6$ tag. Moreover, in *E. coli*, mutant EF-Tu variants with a large C-terminal extension (up to 270 amino acids) were studied and proved to be functional in a strain lacking the chromosomal tufA and tufB genes and, as such, not expressing the native EF-Tu (Schnell et al, FEBS Lett 538:139-144 (2003)). Thus, the C-terminus of EF-Tu, or a short extension of it, is a suitable site for conjugating the quencher molecule.

Structural analysis confirms that the distance from the C-terminus (CA atom) and nucleotide 8 of tRNA (P atom) (this nucleotide is a target for fluorescence labeling) is about 31 Å (FIG. 2), which is very suitable for the FRET assay. The conjugation to the C-terminus may involve additional steps, such as engineering poly-Lys tags and Cys tags on EF-Tu and an implementation of the Lys- and Cys-specific labeling methods.

Standard protocols for labeling primary amino groups on amino acid residues, typically ε-amino groups of lysines can be determined. The quencher molecule can be attached to an EF-Tu:tRNA complex (rather than EF-Tu by itself), followed by the recovery of labeled EF-Tu from the complex, as a way of protecting the tRNA-interacting regions of EF-Tu from labeling. Selected methods to label EF-Tu are set forth in Examples 4-7.

Nucleotide

Guanosine 5'-triphosphate (GTP) allows EF-Tu to bind to tRNA. The nucleotide binding site on EF-Tu is shown in FIG. 2. It comprises the vicinity of EF-Tu's residues Asp21 to Lys24, Lys137 and Leu176. Nucleotide analogs can also bind to this site. For instance, the crystal structure represented in FIG. 2 was obtained using a GTP analog GDPNP (Nissen et al, Science, 270:1464-1472 (1995)). Fluorescent analogs of GTP are also known in the art, including BODIPY FL GTP and BODIPY R6G GTP and trinitrophenyl (TNP) GTP and 2'-(or -3')-O-(N-methylanthraniloyl) guanosine 5'-triphosphate (MANT-GTP). Many other types of dye-derivatized GTP analogs can be synthesized by a person skilled in the art.

The nucleotide is stably bound in the complex aa-tRNA: EF-Tu:GTP and the complex dissociation constant is in the low nanomolar range (Dell et al, Biochemistry 29:1757-1763 (1990)). As shown in FIG. 2, the nucleotide is positioned within 50 Å of many residues in tRNA and, as such, its derivatives can be used in the FRET assay together with derivatized forms of tRNAs (and EF-Tu).

Biochemical Reactions

The mRNA-dependent protein synthesis on the ribosome is utilized in this invention In a typical reaction, tRNA, EF-Tu and the GTP are labeled with a fluorescent dye and a quencher molecule. Because low fluorescence background is desired, a purified translation system can be used.

An example of a fully-configured purified translation system is presented in Shimizu (Shimizu et al, Nat Biotech 19:751-755 (2001)). The system includes 32 components as follows: initiation factors IF1, IF2, IF3; elongation factors EF-G, EF-Tu and EF-Ts; release factors RF1, RF3 (RF2 is not used, for RF2 is not required for the translation of genes terminating with the codons UAG or UAA); termination factor RRF; amino acid synthetases AlaRS, ArgRS, AsnRS, AspRS, CysRS, GlnRS, GluRS, GlyRS, HisRS, IleRS, LeuRS, LysRS, MetRS, PheRS, ProRS, SerRS, ThrRS, TrpRS, TyrRS, ValRS; methionyl-tRNA transformylase MTF; T7 RNA polymerase and ribosomes.

In addition, 46 tRNAs, NTPs, creatine kinase, myokinase, nucleoside-diphospate kinase and pyrophosphate are also present in the reaction mixture. In order to collect sequence data related to only one codon type (and therefore, one tRNA and one amino acid residue), a much simpler translation system can be used. For instance, to translate poly(U) RNA, the following components are needed: preformed Phe-tRNAPhe:EF-Tu-GTP complex; protein factors EF-G and EF-Ts; ribosomes; poly(U); GTP and ATP; phosphoenol pyruvate; pyruvate kinase; myokinase. The reaction conditions for the poly(U) system and other details are set forth in Example 10.

Single Molecule Detection

The fluorescence signals from the translation reaction can be distinguished by using different pairs of fluorescent dyes and quencher molecules and multiparameter analysis of light emitted by the dyes. Many different fluorescent and quencher pairs of molecules are available. The dyes might differ in several fluorescence parameters, such as the wavelength of light emitted by the fluorescent dye, translational diffusion, fluorescence lifetime, molecular energy transfer, molecular brightness, molecular rotation and coincident dual color brightness. Such parameters can measured by analytical instruments, such as for example, Cenfocor II (manufactured by Carl Zeiss, Germany), Insight and Clarina II workstations (manufactured by Evotec Technologies GmbH, Hamburg, Germany) or MicroTime 200 (PicoQuant, Berlin, Germany). Thus, light emitted from a single ribosomal particle can give precise information about the identity of a codon, thus providing the identity of three consecutive nucleotides.

Fluorescent resonance energy transfer (FRET) is a technique generally used for studying conformational distribution and dynamics of biological molecules. Some molecular events or conformational changes are difficult to synchronize or too rare to detect using ensemble FRET. FRET, detected at the level of a pair of single molecules (donor and acceptor), i.e., single-pair FRET (spFRET), opens up new opportunities to probe the detailed kinetics of single-molecule processes without the need for synchronization. SpFRET was applied recently to acquiring sequence information from a synthetic oligonucleotide by Braslavsky (Braslavsky et al, Proc Natl Acad Sci USA 100:3960-3964 (2003)). Three modes of detection are possible in conjunction with spFRET, namely in solution in sub-femtoliter volume, on a surface, in zero-mode waveguides (zero-mode waveguides are sub-wavelength holes in a metal film). The waveguides may be made by nanofabrication techniques and are often mounted on a glass slide. They are a new tool in measuring fluorescence from single molecules (Levine et al, Science 299:682-686 (2003)). The purpose of implementing them is to limit the volume from which the fluorescence signal is acquired. The shape of a single *E. coli* ribosome can be approximated by a sphere having a radius of 25 nm; thus a suitable diameter of the zero-mode wave guide is 30 nm or larger. The use of waveguides of such size was described by Levine; the 30 nm waveguides allow one to work at concentrations as high as 200 μM and still have less than one molecule per volume. Different size waveguides (30-300 nm) can be implemented, depending on the specifications for the chemical reactions and hardware for optical detection.

Assay Options

One of the key aspects of the invention is that the ribosome and translational machinery are employed to sequence nucleic acids. There is a number of possible labeling schemes, involving not necessarily a pair of a fluorescent dye and a quencher molecule, but perhaps only one fluorescent dye (no quencher molecule), or some other combination of fluorescent or fluorescence-modifying molecules. The labeled molecules do not have to be EF-Tu and aa-tRNA; the pair of labeled molecules could be, for example, the ribosome and EF-Tu, or EF-Tu and EF-G. It is conceivable that signal detection could be based on a method other than fluorescence, such as chemiluminescence. The translation mixture could be assembled from cloned and purified molecular components or be prepared from the cell cytoplasm. The molecular components or extract can come from many different prokaryotic or eukaryotic organisms.

Labeling Schemes

Different labeling schemes can support the collection of sequence data in the ribosome system. The general approach is to label components of the macromolecular complex to which the amino acid is bound before it is incorporated into the nascent polypeptide chain. Thus, the choices are aa-tRNA, EF-Tu or the nucleotide (GTP) bound to EF-Tu. According to the present invention, different labeling schemes can be used including, but not limited to, aa-tRNA labeled with the fluorescent dye and EF-Tu with a quencher molecule (shown in FIG. 1); or EF-Tu labeled with a fluorescent dye and aa-tRNA with a quencher molecule (this is the reverse labeling scheme). In addition, the nucleotide can be labeled with either the fluorescent molecule or a quencher molecule, and aa-tRNA or EF-Tu are then labeled with a quencher molecule or fluorescent molecule, respectively.

Although in the reverse labeling scheme, the tagged EF-Tu can dissociate from a complex with tRNA which could be followed by binding to another EF-Tu molecule tagged with a different dye (in more than one-tag systems) (if this happens, false sequence information is obtained at the time the polypeptide chain is extended), the dissociation rate constant for the tRNA-EF-Tu complex is quite low, on the order of $10^{-3}$-$10^{-4}$ s$^{-1}$ (Cai et al, J Biol Chem 275:20308-20314 (2000)). Such a low level of reassociation should be tolerable in the reverse labeling scheme.

The labeling with a quencher molecule (in addition to the fluorescent dye) is significant. One advantage of using a quencher molecule is the reduction of fluorescence background originating from non-productive binding of tRNA-EF-Tu complexes diffusing into the decoding site and dissociating in a proofreading step because of the codon-anticodon mismatch. It can be estimated that there are about 10 non-sequence-specific binding events per one productive event (20 amino acid specificities, but non-uniform abundance of different tRNAs). Another advantage is that the fluorescence background is greatly reduced due to the presence of fluorescently-tagged complexes in solution in the vicinity of the ribosome, allowing the use of higher concentrations of complexes to accelerate the biosynthesis. Thus, having a quencher molecule in the system is highly desirable.

The quenching efficiency in spFRET was up to 90% in the experiment aimed at getting fingerprints of nucleotides (Braslavsky et al, Proc Natl Acad Sci USA 100:3960-3964 (2003)), although it varied greatly as it was heavily dependent on the position within the synthetic oligonucleotide. The efficiency in the spFRET system investigated by Ha (Ha et al, Proc Natl Acad Sci USA 93:6264 (1996)), two dyes linked with a short oligonucleotide) approached 85%. While these numbers provide typical maximum efficiency of quenching in spFRET, it needs to be stressed that the quenching efficiency in a particular implementation of the present invention may vary as the position and orientation of the dyes (fluorophore and quencher) may differ due to the dye-macromolecule linker flexibility and interactions between the dyes and protein surfaces. However, quenching efficiency can be as high as 99.9% as observed in molecular beacons (Tyagi et al, Nat Biotechnol 16:49-53 (1998)), strongly depending on the dyes' relative orientation.

As discussed above, labeling can be accomplished with a fluorescent molecule alone or with a fluorescent molecule and a quencher molecule. When a fluorescent molecule is utilized without a quencher molecule, a fluorescence signal is generated. When a fluorescent molecule and a quencher molecule are utilized together, the fluorescence signal can be observed as result of a decrease in quenching. Both labeling techniques enable the acquisition of sequence information, with the distinction that when a quencher molecule is omitted, a higher background fluorescence is observed. When a quencher molecule is utilized, the fluorescence signal from EF-Tu:tRNA may be reduced by a factor corresponding to the quenching efficiency, while the fluorescence signal from the dissociated components of the EF-Tu:tRNA complex (following codon recognition) may not be reduced. An assay method without a quencher is described in Example 15.

Concentrations of Reagents

The translation system can be configured in such a way that relatively few (preferably one on the average) fluorescent molecules are present in the volume from which the fluorescence signal is acquired. This volume may vary from as little as 100 attoliters in solution, a few tens of attoliters in the assay on a surface, and perhaps as little as 30 zeptoliters ($30 \times 10^{-21}$ liter) in zero-mode waveguides (30 nm across). One molecule in 1 attoliter volume is equivalent to a 1.6 nM concentration, which is significantly less than typical concentrations of EF-Tu in the translation reaction (about 1 μM). The efficient quenching of the fluorescent signal from the tRNA:EF-Tu complex will allow for the increase of the working concentration of EF-Tu in solution by a factor comparable with the quenching efficiency, for example if quenching reduces the fluorescence signal 10-fold, the concentration can be increased by a factor of 10. The implementation of lower concentrations is facilitated by the use of preformed tRNA-EF-Tu complexes (in a typical translation experiment, tRNA and EF-Tu are provided separately). The problem of assuring a sufficiently low concentration of reagents is greatly reduced or eliminated if zero-mode waveguides are used.

Immobilization of the Ribosome

It is important that only one ribosome translates one mRNA molecule at a time, as the translation of one mRNA molecule by two ribosomes or more can lead to an ambiguity in interpreting the fluorescence signals. There are several ways to ascertain that one ribosome is in a complex with one mRNA, for example, (a) reducing the concentration of ribosomes, such that there are many more mRNA molecules than ribosomes, so that no more than one ribosome would be able to find an mRNA, (b) engineering an inefficient ribosome start site into the mRNA molecule being assayed, (c) adjusting buffer composition post-initiation to reduce the likelihood of further ribosomal initiations. Another solution is to bind ribosomes to a surface (see Example 11); in such circumstances multiple initiations are unlikely.

Limitations Due to Wobble

Wobble in codon-anticodon recognition can result in ambiguities in the nucleic acid sequence obtained using the present method. There are 86 tRNAs in *E. coli* decoding standard 20 amino acids based on the sequence analysis of the *E. coli* genome. These 86 tRNAs can be grouped into 39 tRNA specificities in *E. coli*, defined as tRNAs with different anticodon sequences capable of recognizing all coding codons. There is a redundancy in the coverage if one considers wobble rules. It turns out that the minimum set of tRNAs capable of recognizing all codons consists of 31 tRNAs, since three tRNAs per each amino acid type are needed to recognize all codons for Arg, Leu and Ser; two tRNAs—for Ala, Gly, Pro, Thr, Val; and one tRNA each is sufficient to cover all remaining 12 amino acids. Thus, to sequence coding regions on mRNA using the present approach, one would need a set of 31 tRNAs. The resulting nucleic acid sequence will contain ambiguities G/A or C/T where either G or A (or C or T) is expected in the third position of almost all the codons (except for Met and Trp). However, despite the ambiguities, the amino acid sequence would be accurately determined. The frequency of ambiguities could be reduced as a result of tRNA engineering, for example, modifying tRNA anticodons so that they can not wobble (modifications are known that restrict codon-anticodon specificity). Alternatively, different organisms can be searched for tRNAs with a higher codon specificity. A set of 61 tRNAs with high codon specificity would be needed to completely sequence the coding region of a nucleic acid. Yet another possible approach to minimizing the impact of the wobble is to sequence the nucleic acid in not one, but two or more reading frames (up to six reading frames) with three additional tRNAs to suppress stop codons (a total of 34 tRNAs).

Multi-Color Fluorescence Detection

Thirty one tRNA anticodon specificities and a set of 31 fluorescent tags are needed to acquire sequence information equivalent to the protein sequence. Currently, 14 different color Alexa Fluor-type fluorescent tags (plus many other dyes) are available from the Molecular Probes' catalog, although the ability to discriminate between different color dyes might differ for different dyes. Tags of many colors can be configured based on quantum dots, as the color is determined by the size of the quantum dot. An additional way of discriminating between tags is by varying the brightness of the tag, similar to microbead indexing in multicolor beads (as currently practiced by Luminex Corp. and Quantum Dot Corp.). The discrimination can also be based on the fluorescence lifetime, which might additionally be influenced by the quencher molecule's properties.

Moreover, it is not necessary to use a full complement of 31 types of tags. A very limited number of tags, for example, 5 tags, might suffice. To acquire data, in this example, eight translation reactions are performed, each with four different tRNAs tagged with four fluorescent tags and an additional fifth tRNA tagged with the fifth tag, common to all five reactions, for synchronization. Thus, we get four channels of sequence information from eight reactions, i.e., a total of 32 data channels, sufficient in principle to determine the amino acid sequence.

Analogous schemes with a larger number of tRNA specificities could be implemented to obtain the complete, or close to complete (because of wobble), nucleotide sequence information. A DNA sequencing protocol might involve not five (as above), but 16 reactions and a total of 61 data channels when five fluorescent dyes are implemented.

Mammalian Versus Bacterial Translation

The present method employs a bacterial translation system. It will be tested on poly(U) and a synthetic mRNA. Although future applications are anticipated to be directed towards mammalian mRNA, in particular human mRNA, the bacterial translation system should be suitable for that as many mammalian mRNA can be translated in the bacterial translation system and modification of reaction condition can ease the requirements on the translation initiation. In addition, mammalian mRNA can always be engineered to contain bacterial initiation signals through reverse transcription and PCR or re-cloning.

II. EXAMPLES

The following examples illustrate certain aspects of the invention, and it is understood that the methods described in these examples are not intended to be limiting. Further objectives and advantages of the present invention other than those set forth above will become apparent from the examples which are not intended to limit the scope of the present invention.

Examples 1 and 2 illustrate different methods to fluorescently molecule tRNA. Example 3 demonstrates tRNA labeling with a quencher molecule. Examples 4-7 illustrate labeling of EF-Tu with different forms of a quencher molecule. Examples 8 and 9 provide certain biochemical methods and binding reactions involving tRNA and EF-Tu. Examples 10-12 demonstrate a detection of single complexes involving tRNA and EF-Tu. Example 13 describes a construction of a synthetic mRNA template suitable for the assay. An example of a kit is provided in Example 14. Example 15 illustrates the biochemical reaction in which quencher molecules are not used.

Example 1

This Example illustrates fluorescent labeling of tRNA at position 8. A 4-thiouridine base at position 8 ($s^4$U-8) of tRNA$^{Phe}$ (compare FIG. 2) is fluorescently labeled. Specific tRNA$^{Phe}$ from *E. coli* can be purchased from Sigma-Aldrich. 4-thiouridine at position 8 of tRNA$^{Phe}$ is labeled by reaction with tetramethylrhodamine-5-iodacetamide (TMR-5-iodacetamide, Molecular Probes, Inc., Eugene, Oreg.) according to Johnson (Johnson et al, J Mol Biol 156:113-140 (1982)), with a modification by Jia (Jia et al, Proc Natl Acad Sci USA 94:7932-7936 (1997)). Thirty $A_{260}$ units of tRNA is dissolved in 0.7 ml of 48 mM potassium phosphate buffer (pH 8.4), mixed with 2.8 ml of Me$_2$SO containing 3.1 mg of TMR-5-iodacetamide and allowed to react for 6 hrs at room temperature. Following two phenol extractions to remove the non-covalently bound dye, the tRNA is passed over a Sephadex G25 column, concentrated by precipitation with ethanol and dialyzed into 1 mM potassium acetate (pH 5.0), concentrated by ethanol precipitation and dialyzed before storage. It is expected that the final tRNA$^{Phe}$-TMR adduct contains more than 0.94 mol of TMR per mol of tRNA$^{Phe}$.

The labeling of $s^4$U-8 in tRNAs is a general method used to label most *E. coli* tRNAs. Of 45 *E. coli* tRNA sequences in a tRNA database (Sprinzl et al, Nucleic Acids Res 26:148-153 (1998); www.uni-bayreuth.de/departments/biochemie/sprinzl/trna/index.html), 25 species (56%) have 4-thiouridine at position 8 as the only such-modified residue within the sequence. Janiak (Janiak et al, Biochemistry 29:4268-4277 (1990)) labeled four *E. coli* tRNAs (Ala-, Met-m-, Phe- and Val-tRNAs) at position 8. In addition, an inspection of the database (ibid.) indicated that other tRNA specificities carrying $s^4$U-8 can be obtained from alternative microorganisms. Thus, labeling of additional tRNA specificities can utilize the same or a very similar tRNA labeling scheme.

Example 2

This Example illustrates a tRNA charged with fluorescent dye-labeled amino acid. The modified charged lysine tRNA ε-labeled with fluorophore BODIPY-FL is commercially available under the name FluoroTectGreen$_{Lys}$ tRNA (Promega, Madison, Wis.). Using this system, fluorescently labeled lysine residues are incorporated into nascent proteins during translation. The advantage is the efficient incorporation into protein; the disadvantage is that the labeled lysine residues stay in the proximity of the ribosome as a part of the nascent polypeptide chain, thus contributing to the fluorescence background, which increases as the synthesis of the protein progresses.

Example 3

This Example illustrates the labeling of tRNA with undecagold at position 47. Undecagold is a 6,200 da cluster of gold (Au11, particle diameter of 0.8 nm) known to be a very efficient fluorescence quencher (extinction coefficient $\epsilon_{420}$ of 47,000) (Nanoprobes, 2004). It was used previously to label 3-(3-amino-3-carboxypropyl)uridine ($acp^3$-U) at position 47 of tRNA$^{Phe}$ from E. coli (Blechschmidt et al, Eur J Biochem 219:65-71 (1994)). Au$^{11}$-labeled Phe-tRNA$^{Phe}$ forms a ternary complex with EF-Tu and is active in poly(U)-dependent poly-Phe synthesis. Thus, tRNA can be labeled with nanoparticles while its biological activity is preserved. The distance between residue 47 (P atom) in tRNA$^{Phe}$ and EF-Tu's C-terminus is 29 Å (FIG. 2), quite suitable for the FRET assay. Ten out of 45 E. coli tRNAs in the tRNA database carry $acp^3$-U at the homologous position ((http://www.unibayreuth.de/departments/biochemie/sprinzl/trna/index.html)).

The labeling protocol is provided by the manufacturer (Nanoprobes, Yaphank, N.Y.). To tRNA$^{Phe}$ from E. coli in a 20 mM sodium phosphate buffer (pH 7.4), a water solution of sulfo-succinimido-undecagold is added and incubated for 12-18 hrs at 4° C. The conjugate will be isolated by HPLC using Superose 6 gel (Amersham-Pharmacia Biotech) and eluted with 20 mM sodium phosphate (pH 7.4) with 150 mM NaCl. For storage, 0.1% bovine serum albumin and 0.05% sodium azide will be added. The extent of labeling will be determined from the UV/visible spectrum of the conjugate.

Example 4

This Example illustrates the labeling of amino groups on a poly-Lys tag on EF-Tu with a quencher molecule. The procedure involves first constructing a 2-10 residue poly-Lys tag on the C-terminus of EF-Tu, and then taking advantage of the lysines' high accessibility to solvent and derivatizing the lysines with a primary amino group-specific quencher reagent. The constructions are based on an E. coli plasmid pEFTu-10 (Blank et al, Protein Expr Purif 6:637-645 (1995); Ahmadian et al, FEBS Lett 377:253-257 (1991)) expressing T. thermophilus EF-Tu. The plasmid carrying a gene for EF-Tu with a C-terminal extension is constructed by PCR amplification of the EF-Tu gene from the pEFTu-10 plasmid using two PCR primers, one of which (the downstream primer) will carry a sequence encoding for the poly-Lys tag. The gene is recloned into pEFTu-10, replacing the native gene, after restriction digestion with EcoRI and SmaI, and ligation to the EcoRI- and SmaI-cut pEFTu-10. The length of the C-terminal fragment is 20-50 bp. At least four variations of the poly-Lys tag are constructed, having 2, 4, 6 and 8 lysine residues.

The tagged EF-Tu is expressed in E. coli and purified using a published procedure (Blank et al, Protein Expr Purif 6:637-645 (1995)) which involves two chromatographic steps, an anion exchange column (Q-Sepharose) and gel permeation column (Sephacryl S200 HR). Ten liters of E. coli culture are expected to yield more then 80 mg of pure EF-Tu total. QSY-7 ($M_r$ 791, Molecular Probes, Eugene, Oreg.) can be used as a quencher because of its efficient quenching, excellent compatibility with the fluorophore used (TMR, emission maximum for TMR is at 574 nm, absorption maximum for QSY-7 is at 571 nm (Molecular Probes' handbook, http://www.probes.com/handbook), and its availability as a carboxylic acid succinamide ester, which allows for mild conjugation conditions to amine groups on substrates such as proteins and peptides.

The following conjugation procedure is followed. To 100 μl concentrated EF-Tu (>10 mg/ml) in a borate buffer, pH 7.5, 1 mg of dry QSY-7-OSu is added and vortexed to ensure complete dissolution. The reaction is incubated at room temperature for several hours, the exact time chosen to assure the attachment of the quencher molecule to at least one lysine residue and to minimize protein degradation. According to the QSY-7 manufacturer, an overnight incubation is recommended. The conjugated EF-Tu is separated from the unreacted quencher molecule by size exclusion chromatography on a Sephadex G25 column (Amersham-Pharmacia Biotech). The efficiency of conjugation is evaluated by analytical HPLC (measuring $A_{510}$ versus $A_{280}$ of the protein preparation) and by mass spectrometry. The region to which the quencher molecule is attached is determined by HPLC or mass spec analysis of tryptic peptides.

Steps are taken to label preferentially lysines in the C-terminal tag over 21 lysine residues native to T. thermophilus EF-Tu. The anticipated full solvent exposure and the number of Lys residues in the tag allows for preferential labeling. If a fraction of the protein in the preparation is labeled elsewhere, it is not necessarily a predicament as long as the attachment site is within an appropriate distance (<50 Å) from the fluorescent molecule on the tRNA, and the presence of the quencher molecule does not interfere with EF-Tu's binding to tRNA and its activity in translation.

Example 5

This Example illustrates the labeling of Cys residue on C-terminal tag of EF-Tu. An alternative approach involves the design of a C-terminal tag of about 6 amino acid residues, one of which is cysteine. This is the second cysteine residue in T. thermophilus EF-Tu: the other (native) residue is Cys82. The genetic constructions are analogous to the procedure outlined above. Because of the presence and simultaneous labeling of two Cys residues, the labeling conditions are optimized to preferentially label the C-terminal Cys residue. In addition, Cys82 can be converted to a glycine residue before the Cys-tag is constructed, however, the biological activity of EF-Tu, based on the data from E. coli EF-Tu (Anborgh et al, Eur J Biochem 208:251-257 (1992)), could be reduced by 20-70% (which might be acceptable), depending on the importance of Cys82 in the T. thermophilus enzyme. Interestingly, there are bacterial species in which EF-Tu does not contain any cysteine residue (for example, Streptococcus mutans or Mycobacteria leprae) which allows for an option of engineering a C-terminal Cys residue, overexpressing such EF-Tu in E. coli and implementing it in the conjugation and the FRET assay.

The quenching reagent used in conjugation is QSY-7 maleimide ($M_r$ 858; Molecular Probes, Eugene, Oreg.), the absorption spectrum of which is appropriate for the rhodamine dye to be used to label tRNA (see discussion above). EF-Tu is dissolved at 50-100 μM in a 100 mM phosphate buffer, pH 7.5, at room temperature. The reduction of disulfide bonds is performed by adding a 10-fold molar excess of a reducing agent TCEP (tris-(2-carboxyethyl)phosphine hydrochloride, Molecular Probes, Eugene, Oreg.). A 10 mM stock solution of the quencher molecule is dissolved in DMSO immediately prior to use. The stock solution is slowly added to the protein solution at approximately 10-20 molar excess and mixed vigorously. The reaction proceeds for about 2 hours at room temperature. The reaction and stock solution are protected from light and used in an oxygen-free environment to prevent oxidation of thiols. Upon completion of the reaction with the protein, an excess of glutathione is added to consume excess thiol-reactive reagent, thus ensuring that no reactive species are present during the purification step. The conjugate is separated on a gel filtration column (Sephadex G-25). This protocol is from the Molecular Probes handbook (http://www.probes.com/handbook).

Example 6

This Example illustrates the labeling of EF-Tu with undecagold. The labeling principles with undecagold are described in Example 3. In the present example, undecagold is used to label the C-terminus of the Cys tag-bearing EF-Tu as a way to introduce an efficient quencher onto the protein. The labeling protocol is as recommended by Nanoprobes (Yaphank, N.Y.). To a reduced form of EF-Tu in a 20 mM sodium phosphate buffer (pH 6.5), with 150 mM sodium chloride and 1 mM EDTA, a water solution of undecagold-maleimide is added and incubated for 12-18 hrs at 4° C. The conjugate is isolated by HPLC using Amersham-Pharmacia Biotech Superose 6 gel and eluted with 20 mM sodium phosphate (pH 7.4) with 150 mM NaCl. For storage, 0.1% bovine serum albumin and 0.05% sodium azide are added. The extent of labeling is determined from the UV/visible spectrum of the conjugate.

Example 7

This Example illustrates the labeling of EF-Tu with BHQ-10 quencher molecule. A purified preparation EF-Tu (1.5 mg total) is conjugated to one of the "black hole" quencher molecules, BHQ-10 ($M_r$ 702), available from Biosearch Technologies (Novato, Calif.). BHQ-10 was chosen because of its efficient quenching and availability as a carboxylic acid succinamide ester, which allows for relatively mild conjugation conditions to primary amino groups on proteins (typically, ε-amino groups of lysine residues). BHQ-10 has an absorption maximum at 510 nm and is expected to quench fluorescence of dyes that have emission maxima close to 510 nm.

The following conjugation procedure is followed as recommended by the manufacturer of BHQ-10. To 100 µl concentrated EF-Tu (about 3 mg/ml) in 100 mM borate buffer, pH 7.5, 2 mg of dry BHQ-10 is added and vortexed to ensure complete dissolution. The reaction is incubated at room temperature in the dark for 16 hrs. The conjugated EF-Tu is separated from unreacted quencher molecule by size exclusion chromatography on a NAP-5 Sephadex G25 column (Amersham-Pharmacia Biotech). The elution of EF-Tu-quencher molecule conjugate (EF-Tu-Q) is monitored by observing the color of the eluate ($A_{510}$).

Example 8

This Example illustrates the binding reaction involving EF-Tu and tRNA. In this example, we use a modified charged lysine tRNA ε-labeled with a fluorophore BODIPY-FL, commercially available under the name FluoroTectGreen$_{Lys}$ tRNA (Promega, Madison, Wis.). A typical application of this reagent is in protein labeling in a translation reaction. BODIPY-FL has an excitation maximum at 490 nm and an emission maximum at 510 nm, and together with BHQ-10, this fluorophore-quencher pair is very well matched.

The protocol is adapted from Miller and Weissbach (Miller and Weissbach, Methods Enzymol 30:219-232 (1974)). The reaction mixture contains 30 nM tRNA-BODIPY, 1.4 mg/ml phosphoenolpyruvate (PEP, from Sigma-Aldrich), 20 IU/ml pyruvate kinase (from Sigma-Aldrich) and varying amounts of EF-Tu-Q in a binding buffer (50 mM Tris-HCl, pH 7.4, 10 mM $MgCl_2$, 50 mM $NH_4Cl$ and 5 mM dithiothreitol). Pyruvate kinase and PEP are used here to convert GDP bound to EF-Tu to GTP. A significant change of fluorescence is expected to be observed upon addition of EF-Tu, while in the control experiment (no pyruvate kinase and no PEP added) the dependence is expected to be mostly flat.

Example 9

This Example illustrates the formation of Phe-tRNA$^{Phe}$:EF-Tu-GTP ternary complex. The tRNA-TMR from Example 1 is aminoacylated according to standard protocols (Johnson et al, J Mol Biol 156:113-140 (1982)). Aminoacylation assays of tRNA$^{Phe}$ are performed at 37° C. The reaction buffer consists of 2 mM ATP, 5 mM 2-mercaptoethanol, 20 µM phenylalanine, 10 mM $MgCl_2$, 50 mM Tris (pH 7.5), 20 nM tRNA$^{Phe}$-TMR and 20-200 µg/ml purified recombinant PheRS in a total volume of 50 µl. After 30 min, 10-µl aliquots are analyzed by HPLC and mass spectroscopy. If needed, the aminoacylated tRNA. is purified by phenol extraction and ethanol precipitation.

The ternary complex is obtained according to the following protocol (based on Miller and Weissbach, Methods Enzymol 30:219-232 (1974)). Equimolar amounts of aminoacylated tRNA (Phe-tRNA$^{Phe}$-TMR) and quencher-conjugated EF-Tu-Q are mixed in the binding buffer (50 mM Tris, pH 7.5, 5 mM, 10 mM 2-mercaptoethanol and 10 mM $MgCl_2$) together with 50 µg/ml pyruvate kinase (Sigma-Aldrich) and 1 mM PEP and incubated at 37° C. for 30 min. Complex formation is evaluated in a filter binding assay, and in addition, by monitoring fluorescence as a function of time (excitation at 542 nm, emission at 574 nm for TMR). A significant (several-fold) reduction of fluorescence as a result of complex formation is expected.

In addition to a standard ensemble FRET assay, the formation of the tRNA:EF-Tu complex can be monitored by spFRET at a single-molecule level using instrumentation and protocols described in Examples 10 and 11.

Example 10

This Example illustrates the detection of fluorescence at single molecule level: spFRET in solution. The principle involves poly-Phe synthesis in a purified translation system supplemented with EF-Tu-Q and Phe-tRNA$^{Phe}$-TMR and the measurement of fluorescence intensity from the vicinity of a single ribosome. The biochemical steps are adapted from a recent fluorescent study of single ribosomes (Vanzi et al, RNA 9:1174-1179 (2003)).

E. coli Q13 70S ribosomes and 30S and 50S subunits are prepared and activated (Alexander et al, Biochemistry 33:2109-2118 (1994)), combined into the 70S ribosome and purified by fractionation by ultracentrifugation through a linear sucrose concentration gradient. EF-Ts fused to an intein-chitin-binding domain is purified by binding to a chitin column (New England Biolabs, Beverly, Mass.)). Yeast Phe-tRNA synthetase is purified as described (von der Haar, Methods Enzymol 59:257-267 (1979)). Aminoacylation of Phe-tRNA$^{Phe}$ is performed as described above. Reagents are radiolabeled as needed for quantification. High molecular weight poly(U), a template for translation, is purchased from Sigma-Aldrich.

To perform poly-Phe synthesis, 70S ribosomes are preincubated (1 h) with a mixture of 20 µg of Sigma-Aldrich poly(U), 0.2 pmole of commercially available yeast N-AcPhe-tRNA$^{Phe}$ and 5 nmole Phe in 10 µL of polymix (5 mM KH$_2$PO$_4$ at pH 7.3, 95 mM KCl, 5 mM NH$_4$Cl, 5 mM Mg acetate, 0.5 mM CaCl$_2$, 8 mM putrescine, 1 mM spermidine, 1 mM dithiothreitol). Synthesis at room temperature is commenced by the addition of 3.14 pmole of Phe-tRNA$^{Phe}$-TMR, 380 pmole of EF-Tu-Q and 10 µL of factor mix 1 (200 pmole of EF-G, 40 pmole of EF-Ts, 33 nmole of GTP, 20 nmole of ATP, 200 nmole of phosphoenol pyruvate, 5 nmole of Phe, 1 µg of pyruvate kinase and 0.06 µg of myokinase dissolved in polymix and incubated at 30° C. for 15 min before use) and terminated by the addition of 2 µL of 10 mM puromycin (1 h incubation) (Dincbas et al, FEBS Lett 357:19-22 (1995)).

Fluorescence measurements are done on an integrated fluorescence spectroscopy workstation, such as Insight (manufactured by Evotec Technologies, Germany). The microscope configuration includes a 20 mW 458/477/514 nm argon ion laser and two (1 mW 543 and 5 mW 633 nm) HeNe lasers, the C-Apochromat 40×, N.S. 1.2, water immersion objective with a working distance of 0.23 mm, cover slip thickness 0.14-0.18 mm. The detector is a fiber-coupled actively quenched avalanche photodiode, having the 20 MHz time resolution for counting photons. The working volume for single molecule experiments can be under 1 femtoliter. The software suite includes several molecular resolved fluorescence methods, such as FCS, fluorescence intensity distribution analysis, fluorescence cross-correlation spectroscopy and others for a PC running Windows NT 4.0 OS.

The fluorescence signal is due to the spatial separation of the fluorescent molecule (Phe-tRNA$^{Phe}$-TMR) from the quencher molecule (EF-Tu-Q) as a result of the Phe incorporation into the nascent polypeptide on the ribosome. The signal intensity initially quickly grows as the the fluorescent molecule and the quencher molecule are being separated, and is followed by a slower signal decay phase due to diffusion of the fluorophore away from the illuminated region. On the poly(U) template, the fluorescence peaks appear with a regular frequency corresponding to the Phe incorporation into poly-Phe, up to about 10 times per sec (i.e., the translation rate). Minor fluctuation of the time interval between fluorescence peaks is expected due to randomness of the diffusion processes.

Example 11

This Example illustrates the detection of fluorescence at single molecule level: spFRET on surface. The detection of fluorescence signals from a solid surface is the first step towards the parallel detection of fluorescence signals from several ribosomes, which is of significance for high throughput. The approach can also help to constrain the volume from which the fluorescence signal is collected to the immediate vicinity of the surface. The surface of choice is muscovite mica, a highly negatively charged, hydrophilic aluminosilicate whose crystals exhibit a large degree of basal cleavage, allowing them to be split into very thin atomically flat sheets with six-fold symmetry. The experimental steps are adapted from Vanzi (Vanzi et al, RNA 9:1174-1179 (2003)).

Adsorbed ribosomes are prepared by application of 10 nM ribosomes in 15 µL of polymix (see above) to mica (2 cm$^2$) for 5 min, followed by three washes with binding buffer, one with blocking solution (Block Aid from Molecular Probes, Eugene, Oreg.) diluted 1:20 in polymix containing 1.2 U/µL RNA guard RNase inhibitor (Amersham Pharmacia Biotech, Inc.) and 0.5 mM Phe) and three further washes with polymix.

The adsorption of ribosomes is followed by the enzymatic reaction steps described in Example 10.

Compared with the results from the assay in solution (see above), a slow-down is observed due to immobilization of the ribosome. A reduced background fluorescence from tRNA: EF-Tu complexes in the vicinity of the ribosome is also noted.

Example 12

This Example illustrates the detection of Fluorescence at single molecule level: spFRET in zero-mode waveguides.

Zero-mode waveguides are fabricated at a nanofabrication facility equipped with the e-beam lithography instrument. The detailed procedure for fabrication is provided in the appendix to the Levine paper (Levine et al, Science 299:682-686 (2003)) and it involves the coating of extensively cleaned 25 mm$^2$ fused silica substrates with thermally evaporated aluminum to the final film thickness of about 90 nm, spin-coating with electron-beam lithography resist, curing at 170° C. and exposing in a Leica Vector-Beam IV electron-beam lithography system. The pattern consists of an array of dots with varying area dose and nominal dot size (range 30-300 nm). The samples are then dry-etched with chlorine, boron trichloride and hydrogen gasses and the residual resist is removed from the surfaces with oxygen plasma.

The hardware setup for fluorescence measurements is described above, except that circularly polarized light will be used. The zero-mode waveguides will be illuminated from the glass side and data collected for FCS and time trace recordings.

Experimental steps are adapted from Levine (Levine et al, Science 299:682-686 (2003)). Oxygen plasma-treated coverslips with zero-mode waveguide arrays are used to eliminate non-specific binding. The ribosomes are immobilized to glass by applying 10 nM ribosomes in 15 µL of polymix (see above) onto the zero-mode waveguides for 15 min at room temperature. After immobilization, unbound ribosomes are washed away by three washes with binding buffer, one with blocking solution (Block Aid [Molecular Probes, Eugene, Oreg.] diluted 1:20 in polymix containing 1.2 U/µL RNA guard RNase inhibitor (Amersham Pharmacia Biotech, Inc.) and 0.5 mM Phe), and three further washes with polymix. The translation reaction is performed as described in Example 10.

Time trace curves are expected to have peaks corresponding to single extensions of the nascent polypeptide (poly-Phe) spaced by up to 100 ms intervals (10 aa/s synthesis rate). The background fluorescence depends on the size of the zero-mode waveguide.

Example 13

This Example illustrates how a synthetic mRNA template with a defined sequence is implemented to provide a variable time interval between Phe residues' incorporation into protein to help to determine the signal-to-noise ratio. The RNA sequence corresponds to the amino acid sequence of n repeats of FSFSFFSSFFSSFFFSSS (SEQ ID NO: 1), where F=Phe, S=Ser and n~20 to approximate the length of a typical protein. The mRNA is synthesized from a synthetic gene in an transcription reaction with a T7 RNA polymerase. The gene is assembled by DNA ligation in which a single double-stranded synthetic DNA fragment is converted into a multimeric form, and the orientation of the fragment is controlled by restriction sites on the fragment's end. This was described by Mandecki and Bolling (Mandecki and Bolling, Gene 68:101-107 (1988)). The synthetic gene is amplified by PCR using primers which append the promoter and translation start and stop signals to the gene.

Example 14

The following Example illustrates a kit which provides information regarding the positions of UUU (TTT) codons in a particular type of mRNA molecule. The kit includes an translation reaction mixture described in Example 10 under the heading of "Poly(U) synthesis" containing (a) 70S ribosomes and other listed components, but devoid of Phe-tRNA$^{Phe}$; Initiation factors IF1, IF2, IF3; (b) f-methionyl-tRNA$^{Met-f}$; preformed complex composed of Phe-tRNA$^{Phe}$ labeled with a fluorescence label; (c) EF-Tu labeled with a quencher molecule and GTP; and (d) a solid support for conducting the assay.

Examples of suitable solid support include: glass microscope slides, zero-mode waveguides, or other mechanical parts constraining the volume from which fluorescence can be collected to the volume characterized by linear dimensions ranging from 10 nm to 10,000 nanometers.

To conduct the assays, the user of the kit provides mRNA, typically one type of mRNA, mixes it with reagents (a) through (d) above on the solid support (e), and collects the fluorescence signal using a fluorescent microscope-based instrument.

While the foregoing is directed to embodiments of the present invention, other and further embodiments of the invention may be devised without departing from the basic scope thereof, and the scope thereof is determined by the claims that follow.

Example 15

This Example illustrates the biochemical reaction in which quencher molecules are not used to quench the fluorescence signal from the components of the ribosomal translation reaction. The fluorescent reagent is a modified charged lysine tRNA ε-labeled with a fluorophore BODIPY-FL, commercially available under the name FluoroTectGreen$_{Lys}$ tRNA (Promega, Madison, Wis.) (see Example 8 for additional information). The translation reaction components are provided in Example 10. The RNA molecule is poly(A) (Sigma-Aldrich). The translation is performed as described in Example 10. In the reaction, lysine tRNA$_{UUU}$ molecules recognize consecutive AAA codons in the poly(A) molecule, leading to a series of fluorescence signals indicative of the presence of the AAA codons.

The invention claimed is:

1. An assay method for acquiring information on the relative locations of one or more codons on a single ribonucleic acid, the method comprising:
   contacting components including a ribosomal particle comprising a ribosome and the ribonucleic acid with a complex comprising moieties that are aa$^1$-tRNA, EF-Tu and GTP or a functional analog, wherein at least one said moiety is labeled with a fluorescent molecule (label one), wherein aa$^1$-tRNA is a tRNA for first amino acid aa$^1$ that is charged with aa$^1$;
   providing, in conjunction with the contacted components, a ribosomal translation component mixture;
   generating multiple fluorescent signals over time from label one in correlation with (i) incorporations of aa$^1$ into protein pursuant to translation of the ribonucleic acid directed by the ribosomal particle and (ii) resultant separations of the labeled moiety from the complex; and
   detecting in real time the fluorescent signals from label one over a course of time, the detected signals generated from a single said ribosomal particle and result from the separations of the labeled moiety from the complex, to provide information on the relative positions of codons for aa$^1$ on the ribonucleic acid.

2. The method of claim 1, comprising:
   contacting the ribosomal particle with a second complex comprising moieties that are aa$^2$-tRNA, EF-Tu and GTP or a functional analog, wherein at least one said moiety is labeled with another fluorescent molecule (label two), wherein aa$^2$-tRNA is a tRNA for second amino acid aa$^2$ that is charged with aa$^2$, wherein label one and label two have distinguishable fluorescence properties;
   generating a fluorescent signal from label two, distinct from the fluorescent signal from label one, in correlation (i) with the incorporation of aa$^2$ into protein pursuant to translation of the ribonucleic acid directed by the ribosomal particle and (ii) resultant separation of the labeled moiety of the second complex from the second complex; and
   detecting and distinguishing the fluorescent signal from label two, generated from the single said ribosomal particle, to provide information on the relative positions of one or more codons for aa$^2$ on the ribonucleic acid.

3. The method of claim 2, wherein multiple fluorescent signals are generated over time in correlation with instances of aa$^1$ and aa$^2$ incorporation into protein occur, the method

---

SEQUENCE LISTING

<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: Synthetic Amino Acid Sequence

<400> SEQUENCE: 1

Phe Ser Phe Ser Phe Phe Ser Ser Phe Phe Ser Ser Phe Phe Phe Ser
1               5                   10                  15

Ser Ser comprising detecting such fluorescent signals to provide information on the relative positions of codons for aa$^1$ with respect to codons for aa$^2$.

4. The method of claim 3, further comprising separately conducting said method using a second ribosomal particle comprising a ribosome and a said ribonucleic acid so as to separately generate over time multiple fluorescent signals in correlation with instances of incorporation of two amino acids into protein pursuant to translation of the ribonucleic acid directed by the second ribosomal particle and detecting such fluorescent signals to provide information on the relative positions of codons for the two amino acids, wherein one of the two amino acids is aa$^1$ or aa$^2$, and the other is distinct from aa$^1$ and aa$^2$.

5. The method of claim 1, wherein at least one of aa$^1$-tRNA and EF-Tu in the complex is fluorescently labeled.

6. The method of claim 1, wherein one of aa$^1$-tRNA, EF-Tu and GTP or a functional analog is labeled with the fluorescent molecule, and another of aa$^1$-tRNA, EF-Tu and GTP or a functional analog is labeled with a molecule that quenches the fluorescence of the fluorescent molecule.

7. The method of claim 6, wherein the fluorescent molecule is quenched about 2-fold or more when the complex is formed.

8. The method of claim 6, comprising:
contacting the ribosomal particle with a second complex comprising moieties that are aa$^2$-tRNA, EF-Tu and GTP or a functional analog, wherein at least one said moiety is labeled with another fluorescent molecule (label two), wherein aa$^2$-tRNA is a tRNA for second amino acid aa$^2$ that is charged with aa$^2$, and another of aa$^2$-tRNA, EF-Tu and GTP or a functional analog is labeled with a second quencher molecule that quenches the fluorescence of the second fluorescent molecule, wherein label one and label two have distinguishable fluorescence properties;
generating a fluorescent signal from label two, distinct from the fluorescent signal from label one, in correlation with (i) the incorporation of aa$^2$ into protein pursuant to translation of the ribonucleic acid directed by the ribosomal particle and (ii) resultant separation of the labeled moiety of the second complex from the second complex; and
detecting and distinguishing the fluorescent signal from label two, generated from the single said ribosomal particle, to provide information on the relative positions of one or more codons for aa$^2$ on the ribonucleic acid.

9. The method of claim 8, wherein multiple fluorescent signals are generated over time in correlation with instances of aa$^1$ and aa$^2$ incorporation into protein occur, the method comprising detecting such fluorescent signals to provide information on the relative positions of codons for aa$^1$ with respect to codons for aa$^2$.

10. The method of claim 9, further comprising further comprising separately conducting said method using a second ribosomal particle comprising a ribosome and a said ribonucleic acid so as to separately generate over time multiple fluorescent signals in correlation with instances of incorporation of two amino acids into protein pursuant to translation of the ribonucleic acid directed by the second ribosomal particle and detecting such fluorescent signals to provide information on the relative positions of codons for the two amino acids, wherein one of the two amino acids is aa$^1$ or aa$^2$, and the other is distinct from aa$^1$ and aa$^2$.

11. The method of claim 1, wherein one of aa$^1$-tRNA and EF-Tu is labeled with the fluorescent molecule, and another of aa$^1$-tRNA and EF-Tu is labeled with a molecule that quenches the fluorescence of the fluorescent molecule.

12. The method of claim 11, wherein the fluorescent molecule is quenched about 2-fold or more when the complex is formed.

13. The method of claim 11, comprising:
contacting the ribosomal particle with a second complex comprising moieties that are aa$^2$-tRNA, EF-Tu and GTP or a functional analog, wherein at least one of aa$^2$-tRNA and EF-Tu is labeled with another fluorescent molecule (label two), wherein aa$^2$-tRNA is a tRNA for second amino acid aa$^2$ that is charged with aa$^2$, and another of aa$^2$-tRNA and EF-Tu is labeled with a second quencher molecule that quenches the fluorescence of the second fluorescent molecule, wherein label one and label two have distinguishable fluorescence properties;
generating a fluorescent signal from label two, distinct from the fluorescent signal from label one, in correlation with (i) the incorporation of aa$^2$ into protein pursuant to translation of the ribonucleic acid directed by the ribosomal particle and (ii) resultant separation of the labeled moiety of the second complex from the second complex; and
detecting and distinguishing the fluorescent signal from label two, generated from the single said ribosomal particle to provide information on the relative positions of one or more codons for aa$^2$ on the ribonucleic acid.

14. The method of claim 13, wherein multiple fluorescent signals are generated over time in correlation with instances of aa$^1$ and aa$^2$ incorporation into protein occur, the method comprising detecting such fluorescent signals to provide information on the relative positions of codons for aa$^1$ with respect to codons for aa$^2$.

15. The method of claim 14, further comprising further comprising separately conducting said method using a second ribosomal particle comprising a ribosome and a said ribonucleic acid so as to separately generate over time multiple fluorescent signals in correlation with instances of incorporation of two amino acids into protein pursuant to translation of the ribonucleic acid directed by the second ribosomal particle and detecting such fluorescent signals to provide information on the relative positions of codons for the two amino acids, wherein one of the two amino acids is aa$^1$ or aa$^2$, and the other is distinct from aa$^1$ and aa$^2$.

16. The method of claim 2, wherein EF-Tu or GTP of the second complex is labeled with label two or a quencher.

17. The method of claim 2, wherein EF-Tu of the second complex is labeled with label one or a quencher.

18. An assay method for acquiring information on the relative locations of one or more codons on a single ribonucleic acid, the method comprising:
contacting components including a ribosomal particle comprising a ribosome and the ribonucleic acid with a complex comprising moieties that are aa$^1$-tRNA, EF-Tu and GTP or a functional analog, wherein aa$^1$-tRNA is labeled with a fluorescent molecule (label one) or with a molecule that quenches the fluorescence of the fluorescent molecule, wherein if aa$^1$-tRNA is labeled with the quencher, EF-Tu or GTP/functional analog is labeled with the fluorescent molecule, wherein aa$^1$-tRNA is a tRNA for first amino acid aa$^1$ that is charged with aa$^1$;
providing, in conjunction with the contacted components, a ribosomal translation component mixture;
generating multiple fluorescent signals over time from label one in correlation with incorporations of aa$^1$ into protein pursuant to translation of the ribonucleic acid directed by the ribosomal particle;

detecting in real time the fluorescent signals from label one over a course of time, the detected signals generated from a single said ribosomal particle and result from the separations of the labeled moiety from the complex, to provide information on the relative positions of codons for $aa^1$ on the ribonucleic acid;

contacting the ribosomal particle with a second complex comprising moieties that are $aa^2$-tRNA, EF-Tu and GTP or a functional analog, wherein $aa^2$-tRNA is labeled with a fluorescent molecule (label two) or a with a molecule (quencher two) that quenches the fluorescence of label two, wherein if $aa^1$-tRNA is labeled with quencher two, EF-Tu or GTP/functional analog is labeled with label two, wherein $aa^2$-tRNA is a tRNA for second amino acid $aa^2$ that is charged with $aa^2$, wherein label one and label two have distinguishable fluorescence properties;

generating a fluorescent signal from label two, distinct from the fluorescent signal from label one, in correlation with the incorporation of $aa^2$ into protein pursuant to translation of the ribonucleic acid directed by the ribosomal particle;

detecting and distinguishing the fluorescent signal from label two, generated from the single said ribosomal particle, to provide information on the relative positions of one or more codons for $aa^2$ on the ribonucleic acid; and separately conducting said above steps using a second ribosomal particle comprising a ribosome and a said ribonucleic acid so as to separately generate over time multiple fluorescent signals in correlation with instances of incorporation of two amino acids into protein pursuant to translation of the ribonucleic acid directed by the second ribosomal particle and detecting such fluorescent signals to provide information on the relative positions of codons for the two amino acids, wherein one of the two amino acids is $aa^1$ or $aa^2$, and the other is distinct from $aa^1$ and $aa^2$.

19. The method of claim 18, wherein $aa^1$-tRNA is labeled with label one and $aa^2$-tRNA is labeled with label two.

* * * * *